(12) United States Patent
Belotserkovsky

(10) Patent No.: US 6,507,403 B1
(45) Date of Patent: Jan. 14, 2003

(54) GLOSS SENSOR HAVING DIRT BUILDUP COMPENSATION APPARATUS AND METHOD

(75) Inventor: Edward Belotserkovsky, San Francisco, CA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/906,516

(22) Filed: Jul. 16, 2001

(51) Int. Cl.[7] ................... G01N 21/55; G01N 21/47; H01L 27/00
(52) U.S. Cl. ............... 356/445; 356/446; 250/208.1
(58) Field of Search ................. 356/445, 446, 356/448; 250/208.1

(56) References Cited

U.S. PATENT DOCUMENTS

| | | | | |
|---|---|---|---|---|
| 4,260,263 | A | * 4/1981 | Kummer | 356/448 |
| 5,146,097 | A | * 9/1992 | Fujiwara et al. | 250/372 |
| 5,978,441 | A | * 11/1999 | Early | 378/34 |
| 6,362,884 | B1 | * 3/2002 | Okahira et al. | 356/399 |
| 6,380,529 | B1 | * 4/2002 | Bohn | 250/208.1 |
| 2001/0033382 | A1 | * 10/2001 | Preston et al. | 356/445 |
| 2002/0054290 | A1 | * 5/2002 | Vurens et al. | 356/369 |

\* cited by examiner

*Primary Examiner*—Georgia Epps
*Assistant Examiner*—Timothy Thompson

(74) *Attorney, Agent, or Firm*—Burns Doane Swecker & Mathis; Anthony Miologos

(57) ABSTRACT

A gloss sensor is described for optically measuring the gloss of a surface and compensating for dirt buildup on the sensor. The gloss sensor includes a light source and a first collimator for receiving light energy from the light source, forming therein and emitting therefrom a collimated light beam. A first detector is located within the first collimator for developing a reference signal and a beam splitter disposed adjacent the first end of the first collimator for dividing the collimated beam into a first beam and a second beam, the second beam being received by a reflection device. A first mirror is positioned adjacent a first window, the first mirror adapted to reflect the first beam onto a surface to be measured through the first window and further adapted to receive the second beam reflected from the reflection device. A second mirror is positioned adjacent a second window, the second mirror receiving the first beam reflected from the surface to be measured through said second window and the second beam reflected by the first mirror through the first and second windows, the second mirror positioned at and angle to reflect the second beam back to the reflection device. A second collimator is located to receive the first beam reflected from the second mirror including a second light detector located within the second collimator for deriving a detection signal representing a measurement of the gloss of the surface. A third detector is disposed adjacent the reflection device adapted to receive the second beam and derive a compensation signal representing the dirt buildup on the first and second windows and a correction device receiving the reference signal, the detection signal and compensation signal and developing therein a corrected gloss signal representing the gloss of the surface.

12 Claims, 2 Drawing Sheets

GLOSS SENSOR HAVING DIRT BUILDUP COMPENSATION APPARATUS AND METHOD

FIELD OF THE INVENTION

The present invention relates to gloss sensors for measuring the surface characteristics of paper sheets and more particularly to measurement of gloss using a single device which provides compensation for dirt buildup.

DESCRIPTION OF THE RELATED ART

One of the parameters used in determining the quality of a surface is the surface luster or the gloss of the surface. For example, in paper production the various grades of paper having different surface gloss are produced to suit various applications. During paper production, it is desirable to periodically or continuously measure the gloss of the surface of the paper to ensure that the paper surface has the desired gloss.

Typically, the surface gloss of the paper is measured using a gloss gauge during the last step of paper production before the finished paper is packaged as rolls and shipped. The rolls of paper are then shipped to paper products manufacturers, who process the paper sheet in accordance with the intended use.

Devices for determining the gloss of paper surfaces utilize an optical system which measures the intensity of a beam of light reflected from a paper surface. Typically, the gloss of the paper surface is determined by comparing its reflectance to the reflectance of a known gloss standard, such as a glass tile having a polished surface with a known gloss.

Specifically, in measuring the reflectance of the paper surface, light is projected onto the surface, and a sensor which is responsive to the intensity of light is positioned to measure the intensity of the light reflected from the paper surface. The gloss gauge measures the reflectance of the tile surface in the same manner by substituting the tile surface for the paper surface. The reflectance of the paper surface is referenced to the reflectance of the tile surface, thereby providing a measurement of the gloss of the paper surface. In practice, the reflectance measurement of the tile surface is periodically performed, off-sheet and between scans, as the gloss gauge scans back and forth across the paper surface. The gloss gauge is calibrated during each such measurement with the known reflectance of the tile surface.

Two gloss sensor standards have been developed in the industry under this technique. The first standard, outlined under DIN 54502, for regular gloss measurements specifies that the measurements are to be taken using an angle of 75° for the incident light beam from a line perpendicular to the measured surface. For high-gloss measurements, measurements are taken using an angle of 45° for the incident light beam from a line perpendicular to the surface to be measured. If both measurements are to be made, two separate and distinct sensors are generally used. The second standard, outlined under TAPPI T480, specifies that the measurements are to be taken only using an angle of 75° for an incident light beam from a line perpendicular to the measured surface.

One problem associated with the available gloss sensors is their inability to function properly if the sensor windows become dirty. For example, during production a fine paper dust is produced. This fine paper dust coats the reference tile or the sensor windows; thus, when the sensor is reset by scanning the reference tile, or if a light beam is passed through dirty sensor windows, an inaccurate reading is produced. Therefore, the gloss of the paper will not adequately be detected.

Therefore, there is a need for a gloss sensor that is capable of producing accurate gloss measurement results independent of dirt buildup during production.

There is also a need for a gloss sensor that is more compact and that utilizes less parts, requiring less maintenance than presently-available sensors.

SUMMARY OF THE INVENTION

In accordance with one aspect of the present invention there is provided a gloss sensor for optically measuring the gloss of a surface. The gloss sensor includes a light source, a first collimator for receiving the light from the light source and arranged to form a collimated light beam, wherein the collimated light beam is emitted from a first end of the collimator. The gloss sensor further includes: a first detector within the collimator for developing a reference signal; a beam splitter disposed adjacent the first end of the collimator for dividing the collimated beam into a first beam and a second beam, the second beam being received by a reflection device; a first mirror, positioned adjacent a first window, the first mirror adapted to reflect the first beam onto a surface to be measured and further adapted to receive the second beam reflected from the reflection device. A second mirror is positioned adjacent a second window. The second mirror receives the first beam reflected from the surface to be measured and the second beam reflected by the first mirror through the first window and the second windows. The second mirror is positioned at and angle to reflect the second beam back to the reflection device. A second collimator is disposed adjacent the first collimator, wherein the second collimator is positioned to receive the first beam reflected from the second mirror. A second detector is located within the second collimator and is adapted to receive the first beam. A third detector disposed adjacent the reflection device is adapted to receive the second beam.

In accordance with one aspect of the present invention the gloss sensor for measuring the gloss of a surface includes an illumination source and at least two collimators, wherein the illumination source is disposed within one of the two collimators. A first detector is disposed within the first collimator, the first detector adapted to receive a beam emitted from the illumination source. The gloss sensor further including a beam splitter that divides a beam emitted from the illumination source into two separate beams and a means for reflecting the two separate beams. A second detector disposed within the second collimator receives the one of the two beams from the beam splitter with a third detector positioned to receive the other second beam.

In accordance with another aspect of the present invention there is provided a gloss sensor for optically measuring the gloss of a sample surface. The gloss sensor includes: a light source; a first collimator for receiving the light from the light source to form a collimated light beam, wherein the collimated light beam is emitted from a first end the first collimator; a first detector located within the collimator for developing a reference signal and a beam splitter disposed adjacent the first end of the collimator, wherein the beam splitter divides the collimated beam into a first beam and a second beam, the second beam being received by a reflection device. A first mirror positioned adjacent to a first window, reflects the first beam onto a surface to be measured, the first mirror further adapted to receive the second beam reflected from the reflection device. A second mirror positioned adjacent a second window receives the first beam reflected from the surface to be measured and the second beam reflected by the first mirror through the first window and the second window, wherein the second mirror is positioned at and angle to reflect the second beam back to the reflection device. A second collimator disposed adjacent the first collimator is positioned to receive the first beam reflected from the second mirror. A second detector disposed within the second receives the first beam and produces a measurement signal. A third detector disposed adjacent to the reflection device, receives the second beam and produces a dirt compensation beam, and a signal correction means for producing a gloss reading by correcting the measurement signal with the reference signal and the dirt buildup signal.

DETAILED DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
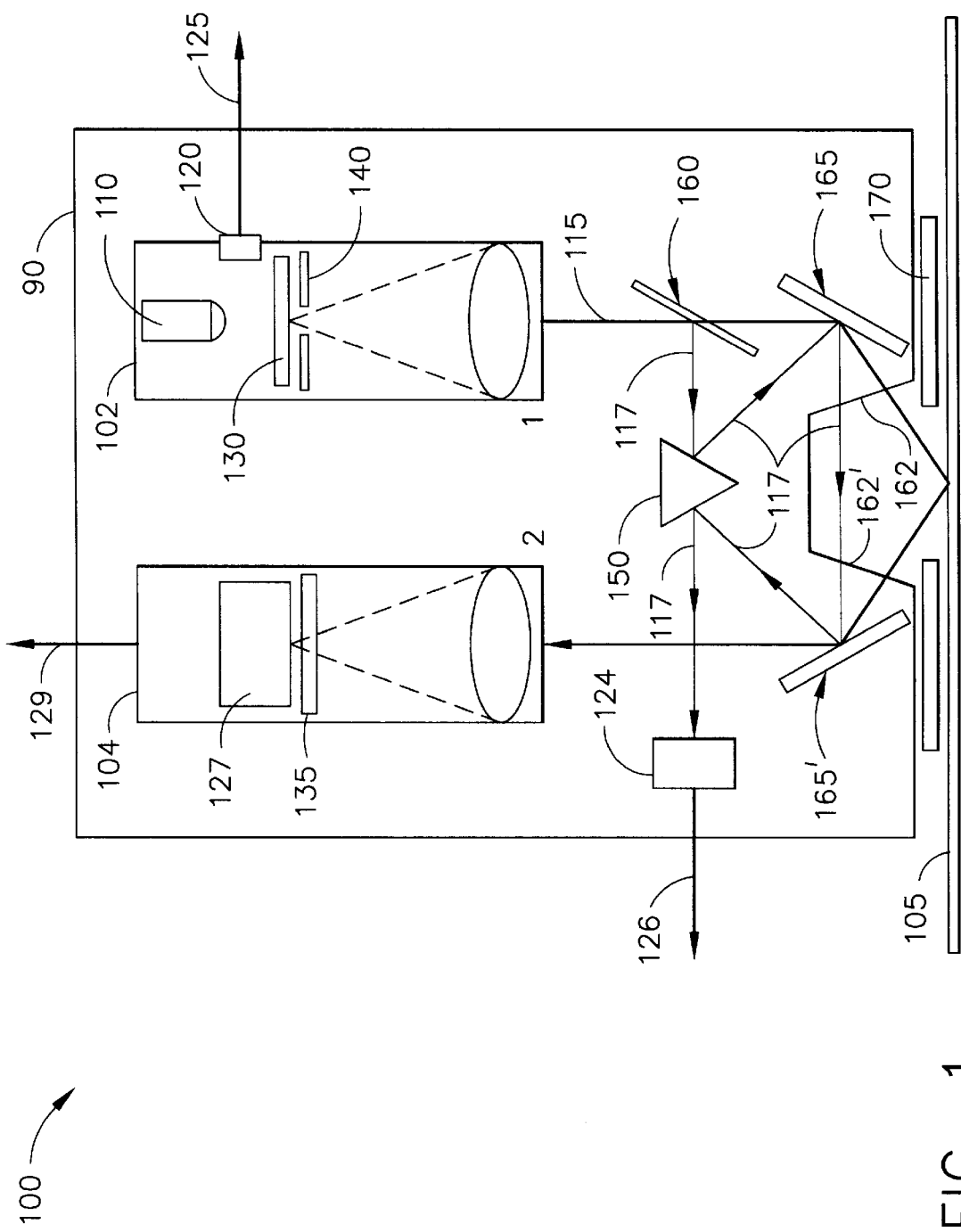
FIG. 1 is a schematic illustration of the gloss sensor of the present invention.

The schematic diagram illustrated in FIG. 1, is a diagram of a gloss sensing system which is positioned to take DIN gloss measurements.

Referring now to FIG. 1 there is shown a diagram of a gloss sensor 100 of the present invention. The gloss sensor 100 includes a first collimator 102, a beam splitter 160, a first mirror 165, a plurality of windows 162 and 162', a second mirror 165', a prismatic reflector 150, a second collimator 104, and an air vortex clamp 170. In addition, the gloss sensor 100 may be provided having a sealed case 90, whereby the entire gloss sensor 100 is shielded from contamination.

The first collimator 102 includes an illumination source 110, a reference detector 120, a diffuser 130, and a diaphragm 140. The second collimator 104 includes a filter 135 and a detector 127. The first collimator 102 and the second collimator 104 are constructed in accordance with DIN 54502 standards.

The light source 110 may comprise an incandescent light bulb, a metal halide light source, a xenon light source, or more preferably an extra bright light emitting diode (LED). The light source 110 is electronically regulated to produce intense radiation in visible (450–650 μm) region, with a peak intensity of about 540–550 nm. The light source may be further regulated to provide light energy having first and second frequencies. The light energy of the first frequency is adapted to pass through the beam splitter 160 with the light energy of the second frequency reflected in a second direction by the beam splitter 160 as will be described in greater detail below. The use of a single light source and a beam splitter 160 allows for a more compact gloss sensor 100. Additionally, due to the less complex design of the gloss sensor of the present invention the overall cost of the gloss sensor 100 may be less than that of presently known comparable gloss sensors.

To provide DIN gloss (75°) measurements in accordance to the DIN 54502 standard, the light energy produced by the light source 110 is collimated by the first collimator 102 into a parallel beam 115. As was explained above, the light energy produced by light source contains light energy of a first and a second frequency. The reference detector 120 disposed within the first collimator 102 transmits a signal 125 containing information regarding the characteristics of the light energy produced by light source 110. The reference signal 125 will be utilized to compare the reflectance of the paper surface to the intensity of the light energy produced by light source 110 with the buildup compensation apparatus shown in FIG. 3 and described in greater detail below.

As shown in FIG. 1, the parallel beam 115 passes through the beam splitter 160, where the light energy of the second frequency is split from the parallel beam 115 into beam 117 and redirected at an angle of approximately 90° to the parallel beam 115. Parallel beam 115 after passing through the beam splitter 160 contains the light energy of the first frequency which is reflected by the mirror 165 toward the paper 105 through window 162. The mirror 165 is set at an angle of approximately 37.5° with respect to a line perpendicular to the measured surface, thereby directing the parallel beam 115 towards the paper 105. The parallel beam 115 is then reflected by the paper 105, wherein the strength of the light energy reflected from the paper surface represents the gloss of the paper surface.

The parallel beam 115 reflected by the paper 105 is received by the second mirror 165' through window 162'. The second mirror 165' is positioned at an angle of approximately 37.5°, and is thereby adapted to direct beam 115 to the second collimator 104. The second collimator 104 condenses the light energy of the parallel beam 115 onto detector 127 after it is passed through the filter 135. As is shown in FIG. 1, the parallel beam 115 is directed at the paper 105 at an angle of approximately 75° with respect to a line perpendicular to the paper's plane. The coefficient of reflection from the paper surface 105 is proportional to paper gloss.

Figure 3:
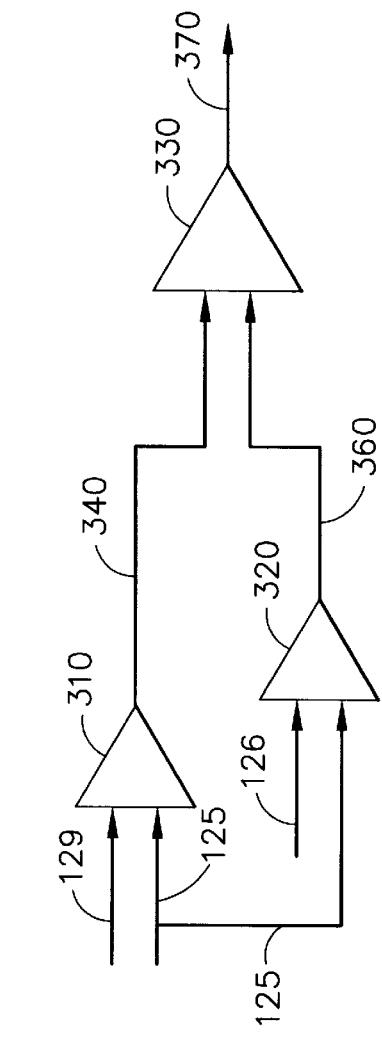
FIG. 3 is a functional diagram of the dirt build-up correction mechanism of the present invention.

The gloss sensor 100 of the present invention further includes a dirt buildup compensation device. The dirt buildup compensation device comprises a prismatic reflector 150, a window detector 124, and a plurality of combining devices 310, 320, and 330 (combining devices 310, 320 and 330 are shown in FIG. 3). As shown in FIG. 1, the beam splitter 160 splits the light energy of the second frequency contained in parallel beam 115 into a beam portion 117 that is at an angle of approximately 90° to the parallel beam 115. The beam 117 is reflected by prismatic reflector 150 to the mirror 165. Beam 117 is then reflected by the mirror 165 through the two windows 162, 162'. The beam 117 is then reflected by the mirror 165' such that the beam 117 is received by the prismatic reflector 150 and reflected to the window detector 124. Window detector 124 develops a dirt buildup compensation signal 126 for use as described in detail below. The prismatic reflector 150 is adjustable within the gloss sensor 100 so the angles of reflection of the second beam 117 may be adjusted accordingly.

As shown in FIG. 1, three distinct signals are developed by the gloss sensor 100, of the present invention including two reference signals and one measurement signal. The first reference signal 125 is developed within the first collimator 102. The second reference signal is developed by the window detector 124, as the dirt buildup compensation signal 126. As shown in FIG. 1, signal 126 originates from beam 117 and is utilized to measure the amount of dirt buildup on the windows 162, 162'. A third signal 129 is a measurement signal developed within the second collimator 104, by the detector 127.

Figure 2:
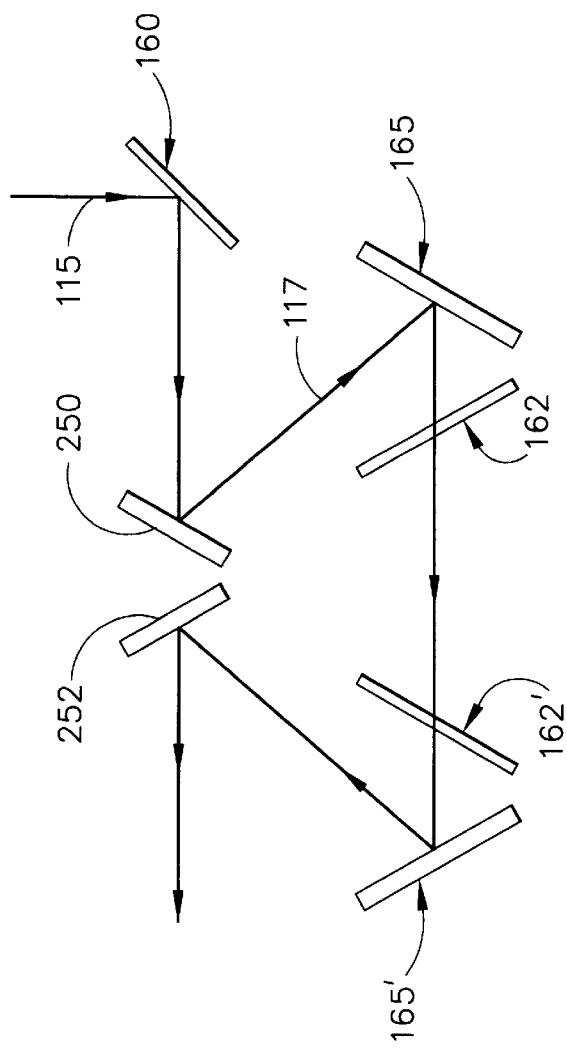
FIG. 2 is a schematic illustration of an alternative embodiment of a buildup correction system for the gloss sensor of the present invention.

Referring now to FIG. 2, there is shown an alternative embodiment of the dirt buildup correction mechanism 300 of the present invention. As shown in FIG. 2, the prismatic reflector 150 of the gloss sensor 100 has been replaced with mirrors 250 and 252. The mirrors 250 and 252 are adjustable so that the proper angle of reflection of the beam 117 can be adjusted accordingly.

Referring now to FIG. 3, there is shown a functional diagram illustrating the function of the dirt buildup correction device 300 of the present invention. The correction device 300 includes a first combining device 310, a second combining device 320 and a third combining device 330. Each of the combining devices 310, 320 and 330 is adapted to receive the signals generated by the detectors of the gloss sensor 100. As shown in FIG. 3, the first combining device 310 receives the resulting measurement signal 129 and the first reference signal 125. Signals 129 and 125 are combined by the combining device 310 and output as signal 340. The output signal 340 represents the measurement of the uncorrected gloss of the paper 105. The second combining device 320 is adapted to receive the dirt buildup compensation signal 126 indicative of dirt buildup on windows 162 and 162' and the first reference signal 125. Signals 126 and 125 are combined by the second combining device 320 and output as a dirt correction signal 360. The uncorrected gloss signal 340 and the dirt correction signal 360 are then received by combining device 330 and output as a corrected gloss signal 370.

The dirt buildup compensation signal 126 having passed through windows 162 and 162' contains information regarding the buildup of dirt on the windows. For example, during the paper making process, dust may build up on the windows 162 and 162'; and, therefore, if the gloss measurement signal was not corrected for this dust buildup, measurement signal 129 would not accurately represent the gloss measurement. Signal 126 also compensates for the dust in the air which may alter the measurement of signal 129.

As a result of the dirt compensation device 300, the gloss sensor 100 of the present invention does not require a standardization procedure as described in detail below. Furthermore, the gloss sensor 100 does not require a standardization mechanical unit; therefore, the gloss sensor 100 may be made more compact than existing sensors with fewer moving parts typically found in presently known gloss sensors.

Typically a standardization unit (nor shown) may be comprised of a known glossy surface whereby the gloss sensor or the known glossy surface is moved so that the gloss sensor will take a reading of the known glossy surface. For example, the known glossy surface may comprise a tile, whereby the gloss sensor would be moved from a position disposed over a paper surface to a position disposed over the glossy surface where the gloss sensor would be calibrated according to the known glossy surface. Alternatively, the standardization unit may comprise a second light source, or a light pipe originating from the first light source, where the light source is directed at an angle to a known glossy surface, wherein the reflection is received by a detector. This signal is then utilized to calibrate the gloss sensor accordingly.

In an alternative embodiment (not shown) the parallel beam 115 and beam 117 may be modulated with two different frequencies $f_1$ and $f_2$ in order to separate the gloss and dirt build-up measurements.

The gloss sensor 100 of the present invention may also be utilized to accurately measure the smoothness of the paper surface. As will be well understood by those skilled in the art, the smoothness of a paper surface can also be correlated to the gloss of the paper.

Further, although the present invention has been described as a sensor for making a high-gloss measurement (75° relative to a line perpendicular to the plane of the paper) the apparatus and methods of the present invention can also be effectively utilized for making standard gloss measurements. Standard gloss measurements are made at an angle of 45° relative to a line perpendicular to the plane of the paper by repositioning and/or relocating mirrors 165, 165' so as to direct and collect parallel beam 115 at an angle of 45° relative to a line perpendicular to the plane of paper 105. Additionally, the elements of the gloss sensor 100 of the present invention, may be duplicated thereby making a gloss sensor that is capable of making both gloss (45°) and high-gloss (75°) measurements simultaneously or at a cyclic rate.

It will be well understood by those skilled in the art that the gloss sensor 100 of the present invention may be further modified to provide gloss measurements at 20°, 60°, and 80° according to ISO 2.813 standards or TAPPI 75° measurement according to the TAPPI T480 standard.

Although the present invention has been described with regard to specific embodiments, it will be apparent to one skilled in the art that the various changes and modifications can be made and equivalents employed without departing from the present invention.

What is claimed is:

1. A gloss sensor for optically measuring the gloss of a sample surface, the gloss sensor comprising:
   a light source;
   a first collimator for receiving the light source to form a collimated light beam, wherein the collimated light beam is emitted from a first end of the first collimator;
   a first detector within the first collimator for developing a reference signal;
   a beam splitter disposed adjacent the first end of the collimator, wherein the beam splitter divides the collimated beam into a first beam and a second beam;
   a reflection device for receiving the second beam;
   a first mirror, positioned adjacent to a first window, to reflect the first beam onto a surface to be measured, the first mirror further positioned to receive the second beam reflected from the reflection device;
   a second mirror, positioned adjacent to a second window, to receive the first beam reflected from the surface to be measured and to receive the second beam reflected by the first mirror through the first window and the second window, wherein the second mirror is positioned at an angle to reflect the second beam back to the reflection device;
   a second collimator positioned to receive the first beam reflected from the second mirror;
   a second detector disposed within the second collimator, wherein the second detector is adapted to receive the first beam; and
   a third detector disposed adjacent to the reflection device, wherein the third detector is adapted to receive the second beam.

2. The gloss sensor according to claim 1, wherein said illumination source comprises an extra bright light emitting diode.

3. The gloss sensor according to claim 2, wherein the illumination source is electronically modulated to produce an intense radiation having a peak intensity between about 540 nm and 550 nm.

4. The gloss sensor according to claim 3, wherein the intense radiation is produced in the visible region between about 450 μm and about 650 μm.

5. The gloss sensor according to claim 1, wherein said illumination source comprises a metal halide bulb.

6. The gloss sensor according to claim 1, wherein said illumination source comprises a xenon gas-charged source.

7. The gloss sensor according to claim 2, wherein the light source is modulated to produce a first frequency and a second frequency, wherein the first frequency is the first beam and the second frequency is the second beam.

8. The gloss sensor according to claim 1, wherein the reflection means is a prismatic reflector.

9. The gloss sensor according to claim 8, wherein the prismatic reflector is adjustable.

10. The gloss sensor according to claim 1, wherein the reflection means is a plurality of adjustable mirrors.

11. A gloss sensor for optically measuring the gloss of a sample surface, the gloss sensor comprising:

a light source;

a first collimator for receiving the light source to form a collimated light beam, wherein the collimated light beam is emitted from a first end of the first collimator;

a first detector within the first collimator for developing a reference signal;

a beam splitter disposed adjacent the first end of the collimator, wherein the beam splitter divides the collimated beam into a first beam and a second beam;

a reflection device for receiving the second beam;

a first mirror, positioned adjacent to a first window, to reflect the first beam onto a surface to be measured, the first mirror further positioned to receive the second beam reflected from the reflection device;

a second mirror, positioned adjacent to a second window, to receive the first beam reflected from the surface to be measured and to receive the second beam reflected by the first mirror through the first window and the second window, wherein the second mirror is positioned at an angle to reflect the second beam back to the reflection device;

a second collimator positioned to receive the first beam reflected from the second mirror;

a second detector disposed within the second collimator, wherein the second detector is adapted to receive the first beam and to produce a measurement signal;

a third detector disposed adjacent to the reflection device, wherein the third detector is adapted to receive the second beam and produce a dirt compensation signal; and a signal correction means for producing a gloss reading by correcting the measurement signal with the reference signal and the dirt compensation signal.

12. The gloss sensor according to claim 1, wherein the second collimator is disposed adjacent the first collimator.

* * * * *